(12) United States Patent
Sun

(10) Patent No.: US 7,365,330 B1
(45) Date of Patent: Apr. 29, 2008

(54) METHOD FOR THERMAL TOMOGRAPHY OF THERMAL EFFUSIVITY FROM PULSED THERMAL IMAGING

(75) Inventor: Jiangang Sun, Westmont, IL (US)

(73) Assignee: UChicago Argonne, LLC, Chicago, IL (US)

( * ) Notice: Subject to any disclaimer, the term of this patent is extended or adjusted under 35 U.S.C. 154(b) by 82 days.

(21) Appl. No.: 11/522,757

(22) Filed: Sep. 18, 2006

(51) Int. Cl.
*G01J 5/58* (2006.01)

(52) U.S. Cl. .......................... 250/341.6; 374/5
(58) Field of Classification Search ............... 250/341.6
See application file for complete search history.

(56) References Cited

U.S. PATENT DOCUMENTS

| | | | |
|---|---|---|---|
| 5,711,603 A * | 1/1998 | Ringermacher et al. | 374/5 |
| 6,367,969 B1 * | 4/2002 | Ringermacher et al. | 374/7 |
| 6,517,236 B2 | 2/2003 | Sun et al. | |
| 6,542,849 B2 | 4/2003 | Sun | |
| 6,712,502 B2 * | 3/2004 | Zalameda et al. | 374/5 |
| 6,730,912 B2 | 5/2004 | Sun et al. | |
| 7,018,094 B1 * | 3/2006 | Bates | 374/121 |
| 2005/0008215 A1 * | 1/2005 | Shepard | 382/141 |

* cited by examiner

*Primary Examiner*—David P. Porta
*Assistant Examiner*—Marcus H Taningco
(74) *Attorney, Agent, or Firm*—Joan Pennington

(57) ABSTRACT

A computer-implemented method for automated thermal computed tomography includes providing an input of heat, for example, with a flash lamp, onto the surface of a sample. The amount of heat and the temperature rise necessary are dependent on the thermal conductivity and the thickness of the sample being inspected. An infrared camera takes a rapid series of thermal images of the surface of the article, at a selected rate, which can vary from 100 to 2000 frames per second. Each infrared frame tracks the thermal energy as it passes from the surface through the material. Once the infrared data is collected, a data acquisition and control computer processes the collected infrared data to form a three-dimensional (3D) thermal effusivity image.

20 Claims, 12 Drawing Sheets

| Hole | Diameter (mm) | Depth (mm) |
|---|---|---|
| A | 7.5 | 0.25 |
| B | 7.5 | 1.12 |
| C | 7.5 | 0.97 |
| D | 7.5 | 0.87 |
| E | 5.0 | 0.78 |
| F | 2.5 | 0.85 |
| G | 1.0 | 0.85 |

METHOD FOR THERMAL TOMOGRAPHY OF THERMAL EFFUSIVITY FROM PULSED THERMAL IMAGING

The United States Government has rights in this invention pursuant to Contract No. W-31-109-ENG-38 between the United States Government and Argonne National Laboratory.

FIELD OF THE INVENTION

The present invention relates to an improved method for analyzing materials, which may be multilayer and inhomogeneous, from one-sided pulsed thermal imaging. More specifically this invention relates to a method for thermal computed tomography from one-sided pulsed thermal imaging. Still more specifically this invention relates to a method and computer program product for automated 3D imaging of subsurface material properties by one-sided pulsed thermal imaging.

DESCRIPTION OF THE RELATED ART

Pulsed thermal imaging is widely used for nondestructive evaluation (NDE) of advanced materials and components. The premise is that internal flaws, such as, disbonds, voids or inclusions, affect the flow of heat from the surface of a solid.

For example, U.S. Pat. No. 6,517,236 issued Feb. 11, 2003 to Jiangang Sun, William A. Ellingson, and Chris M. Deemer discloses a method and apparatus for automated non-destructive evaluation (NDE) thermal imaging tests of combustor liners and other products. The apparatus for automated NDE thermal imaging testing of a sample includes a flash lamp positioned at a first side of the sample. An infrared camera is positioned near a second side of the sample. A linear positioning system supports the sample. A data acquisition and processing computer is coupled to the flash lamp for triggering the flash lamp. The data acquisition and processing computer is coupled to the infrared camera for acquiring and processing image data. The data acquisition and processing computer is coupled to the linear positioning system for positioning the sample for sequentially acquiring image data.

U.S. Pat. No. 6,542,849 issued Apr. 1, 2003 to Jiangang Sun discloses a method and apparatus for determining the thickness of a sample and defect depth using thermal imaging in a variety of plastic, ceramic, metal and other products. A pair of flash lamps is positioned at a first side of the sample. An infrared camera is positioned near the first side of the sample. A data acquisition and processing computer is coupled to the flash lamps for triggering the flash lamps. The data acquisition and processing computer is coupled to the infrared camera for acquiring and processing thermal image data. The thermal image data are processed using a theoretical solution to analyze the thermal image data to determine the thickness of a sample and defect depth.

A problem is that current thermal imaging methods typically only process the surface temperature in temporal domain to determine one or several parameters under the surface (not a distribution) based on a model of the material system and the defect type.

These methods are considered 2D methods because they can only determine a limited number of parameters under each surface position (corresponding to a pixel in a 2D image). For example, several methods were developed to detect crack (or delamination) depth under the surface and the predicted depths at all surface positions are usually presented in a 2D image corresponding to the surface.

Another problem is that many known methods rely on physical models of the specific material system under study and determine characteristic variables (e.g., time) or fit model parameters to derive the unknown parameters. In particular the material system configuration must be specified in advance (e.g., 1-layer or multi-layer system and defect type) and the material within each layer must be homogeneous.

U.S. patent application Ser. No. 11/452,156 filed Jun. 13, 2006, by the present inventor Jiangang Sun and assigned to the present assignee, entitled "OPTICAL FILTER FOR FLASH LAMPS IN PULSED THERMAL IMAGING" discloses an optical filter made from a borosilicate optical material for flash lamps used in pulsed thermal imaging. The filter substantially eliminates the infrared radiation from flash lamps to allow for accurate detection of surface temperature during entire pulsed thermal imaging tests.

U.S. patent application Ser. No. 11/452,052 filed Jun. 13, 2006, by the present inventor Jiangang Sun and assigned to the present assignee, entitled "METHOD FOR ANALYZING MULTI-LAYER MATERIALS FROM ONE-SIDED PULSED THERMAL IMAGING" discloses a method for multilayer materials that was developed to determine multiple material parameters including conductivity, optical transmission, and thickness and/or crack depth for each layer.

Thermal tomography methods to provide 3D imaging have been proposed by a number of researchers but none of the proposed methods provide an effective tomographic method.

A principal aspect of the present invention is to provide a method for thermal computed tomography from one-sided pulsed thermal imaging.

Another aspect of the present invention is to provide a method and software for fast 3D imaging of subsurface material properties by one-sided pulsed thermal imaging.

Other important aspects of the present invention are to provide such method for thermal computed tomography from one-sided pulsed thermal imaging substantially without negative effect and that overcome some of the disadvantages of prior art arrangements.

SUMMARY OF THE INVENTION

In brief, a method provides thermal tomography of subsurface material distribution, and is achieved by converting the temporal surface temperature data into a spatial depth distribution of thermal effusivity under the surface.

The method of the invention includes providing an input of heat, for example, with a flash lamp, onto the surface of a sample or article to be examined. The amount heat and the temperature rise necessary are dependent on the thermal conductivity and the thickness of the material being inspected. An infrared camera then takes a rapid series of thermal images of the surface of the article, at a selected rate, which can vary from 100 to 2000 frames per second. Each infrared frame tracks the thermal energy as it passes from the surface through the material. Once the infrared data is collected, it is processed to form a three-dimensional (3D) image.

In accordance with features of the invention, the method advantageously provides 3D image of an article that can be provided in a very short period of time, that is, in a range of a few minutes or less than one minute. The defects and their depths can be seen in the generated 3D image with good image resolution.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

Figure 1:
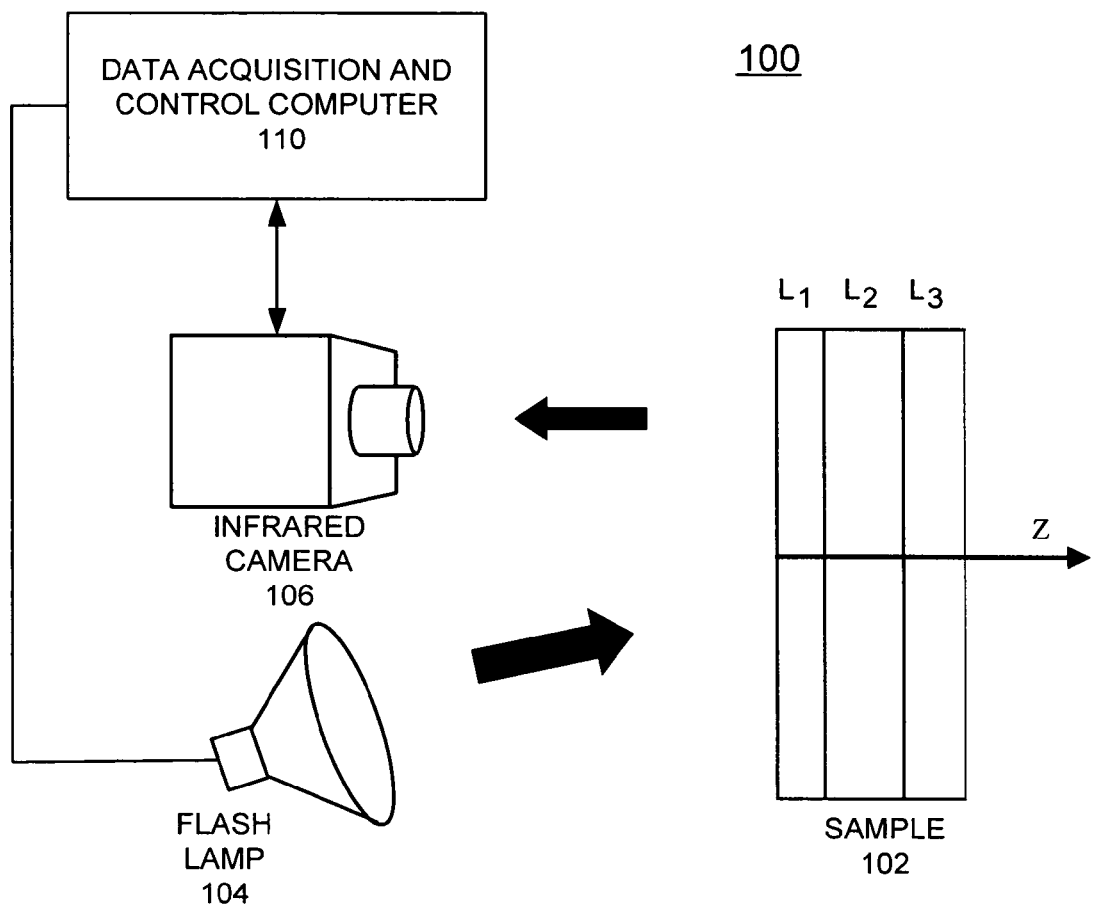
FIG. 1 is a diagram illustrating a thermal imaging apparatus for implementing a method for thermal computed tomography from one-sided pulsed thermal imaging in accordance with the preferred embodiment.

In accordance with features of the invention, a thermal tomography method converts the temporal series of 2D surface temperature data into a spatial 3D distribution of material effusivity under the surface.

In comparison, conventional thermal imaging methods only process the surface temperature in temporal domain to determine one or a few parameters at each surface position (a pixel in a 2D image) based on a model of the material system; these methods are considered 2D methods because they cannot provide the distribution of material property under the surface. For example, several methods were developed to detect crack, or delaminations, depth under the surface and the predicted depths at all surface positions are usually presented as a 2D depth map for the surface. Recently, a method for multi-layer materials was developed by the present inventor to determine multiple material parameters including conductivity, optical transmission, and thickness and/or crack depth for each layer. In principle, this method can determine as many material parameters as needed, and each predicted parameter could be plotted into a 2D image mapped over the specimen surface. However, all these methods rely on physical models of the specific material system under study and determine characteristic variables, for example, time, or fit model parameters to derive the unknown parameters. These methods cannot resolve superimposed features along depth and can usually detect only one dominant feature under the surface. In particular, the material system configuration must be specified first in order to select an appropriate model for the system, for example, 1-layer or multi-layer system, and the material within each layer must be homogeneous. These methods are therefore not suitable to characterize materials with inhomogeneous material properties in the depth direction. One example of such material system is the human skin.

Theoretical development of this invented method is now described based on typical 1D solutions of the heat conduction equation under pulsed thermal imaging condition.

Theoretical Development

The 1D governing equation for heat conduction in a solid material is represented by the following equation (1):

$$\rho c \frac{\partial T}{\partial t} = \frac{\partial}{\partial z}\left(k \frac{\partial T}{\partial z}\right), \quad (1)$$

where $T(z,t)$ is temperature, $\rho$ is density, c is specific heat, k is thermal conductivity, t is time, z is coordinate in the depth direction, and z=0 is the surface that receives flash heating. It is noted that Eq. (1) contains only two independent thermal parameters, the heat capacity $\rho c$ and the thermal conductivity k, both may vary with depth z, but are treated constant in the following derivations.

During flash thermal imaging, an impulse energy Q is applied on surface z=0 at t=0. An ideal condition is assumed for the following derivation, i.e., (1) flash is instantaneous or flash duration is zero and (2) flash heat is absorbed at a surface layer of zero thickness. Other than the flash heating, all surfaces are assumed to be insulated at all times. After the surface at z=0 receives initial heating and reaches a high temperature (theoretically to infinity with the instantaneous heating), heat conduction takes place in the z (or depth) direction. For a semi-infinite material ($0 \leq z \leq \infty$), the solution of surface temperature from the governing equation (1) under the ideal condition is:

$$T(t) = T(z=0, t) = \frac{Q}{(\rho c k \pi t)^{1/2}} \quad (2)$$

where T(t) is the surface temperature that is continuously measured by an infrared detector (a pixel in an infrared imaging array) during the thermal imaging test. It is seen that there is a single (combined) material thermal property in Eq. (2) which is commonly defined as thermal effusivity $e=(\rho c k)^{1/2}$ Equation (2) can be rearranged as:

$$e_a = \frac{Q}{T(t)\sqrt{\pi t}} \quad (3)$$

where $e_a$ is called the apparent thermal effusivity. Equation (3) can be generalized as the definition for apparent effusivity, with T(t) as the surface temperature measured from an arbitrary sample during a pulsed thermal imaging test (not only for semi-infinite medium as it was originally defined from). Because the deposited heat Q is a constant (which can be measured), $e_a$ in general is a function of time, i.e., $e_a=e_a(t)$. From Eqs. (2) and (3), it is seen that $e_a(t)$ is a constant and equals to the material effusivity $(\rho c k)^{1/2}$ for semi-infinite single-layer materials. However, $e_a(t)$ normally differs from the material effusivity for multi-layer and/or inhomogeneous materials.

Equation (3) converts the measured surface temperature into an apparent effusivity which is related to the real thermal effusivity of the sample's interior. In order to establish a formulation between the time-dependent apparent effusivity with the spatial-dependent material effusivity, it is necessary to determine the relationship between time and space under pulsed thermal imaging condition (or to determine the speed of heat transfer). For this purpose, we examine another solution. For a finite-thickness plate ($0 \leq z \leq L$), the surface temperature solution from the governing Eq. (1) is $$T(t) = T(z=0, t) = \frac{Q}{\rho c L}\left[1 + 2\sum_{n=1}^{\infty} \exp\left(-\frac{n^2\pi^2}{L^2}\alpha t\right)\right] \quad (4)$$

where $\alpha$ ($=k/\rho c$) is thermal diffusivity which is commonly understood to be relevant to the speed of heat conduction in transient heat transfer process. Note that the parameter $\alpha t/L^2$ is a nondimensional parameter, or it can be considered as a parameter that relates the temporal time t with spatial distance L. The present invention has identified a unique relationship determined from Eq. (4) under the constraint $d^2(\ln T)/d(\ln t)^2=0$, which is: $L=(\pi\alpha t)^{1/2}$. This can also be generalized to:

$$z=(\pi\alpha t)^{1/2} \quad (5)$$

Equation (5) is assumed to be the general relationship between spatial distance z and time t for heat transfer process. It also indicates that the heat-transfer "speed" dz/dt varies (or decreases) with time. The material parameter that determines the heat transfer "speed" is the thermal diffusivity $\alpha$.

The final step in the development of this thermal tomography method is to derive the solution for the spatial distribution of the material thermal effusivity from the time-dependent apparent effusivity defined in Eq. (3). In this invention, it is postulated that the measured apparent effusivity at a certain time t corresponds directly to the averaged material effusivity within a certain depth z, where z and t are related by Eq. (5). This postulation converts the temporal-domain apparent effusivity into the spatial-domain depth distribution of the actual material effusivity. Physically, it emphasizes the fact that heat conduction is a finite-speed process with heat being deposited along its propagation path, so surface information at a certain time can only come from the material information within a finite depth that heat has propagated through within that time period. In this invention, however, the diffusive/dissipative nature of the heat transfer process is not addressed (the leading edge of the heat propagation gradually diffuses); it will be a topic of future studies. Based on this postulation, we have:

$$e_a(t) = \frac{1}{z}\int_0^z e(z)\,dz. \quad (6)$$

It is recognizable that Eq. (6) is a simple convolution formulation, with a convolution kernel function of unity within the integral. In discrete-increment form, Eq. (6) can be expressed as:

$$e_a(t_n) = \frac{\sum_{i=1}^{n} e_i \Delta z_i}{\sum_{i=1}^{n} \Delta z_i}, \quad \text{and } z_n = \sqrt{\pi\alpha t_n} = \sum_{i=1}^{n} \Delta z_i \; n=1, 2, 3, \ldots \quad (7)$$

where $e_i=e(z_i)$ is a spatial distribution function. When the increment $z_i$ is constant, we have:

$$e_a(t_n) = \frac{1}{n}\sum_{i=1}^{n} e_i \; n=1, 2, 3, \ldots \quad (8)$$

Therefore, $e_n$ can be solved from:

$$e_n = e(z_n) = ne_a(t_n) - \sum_{i=1}^{n-1} e_i \; n=1, 2, 3\ldots \quad (9)$$

where $z_n=(\pi\alpha t_n)^{1/2}$ with $\alpha$ being the thermal diffusivity. It is seen that the deconvolution formulation Eq. (9) is explicit, so it can be calculated very efficiently.

In brief, this invention provides a completely new approach to process thermal imaging data so, for the first time, 3D imaging of entire sample volume is achieved. It is based on several postulations and generalizations of simple solutions of the governing heat transfer equation under pulsed thermography test condition. In particular, the invention consists of three findings or components.

(1) It identified that the thermal effusivity $e=(\rho c k)^{1/2}$, which is related to the thermal impedance of a material, is a suitable imaging parameter to construct the 3D image of the test material.

(2) This invention determined a relationship between the space (depth) and the time, i.e., $z=(\alpha\pi t)^{1/2}$, which shows that the "speed" dz/dt of heat propagation is related to the thermal diffusivity and time so it is not constant for each material but decreases with time.

(3) This invention has established a deconvolution algorithm to solve the depth profile of the material thermal effusivity from the measured surface temperature data. The predicted effusivity is a direct function of depth, not an average or convolved parameter, so it is an accurate (and more sensitive) representation of local property along depth. In conventional (2D) thermal imaging methods, however, final results are usually presented in images of the measured surface temperature T(t) (including its derivatives) and apparent effusivity $e_a$, these data are difficult to be used to interpret the detailed structures within the material.

The governing heat conduction equation (1) contains two independent thermal properties, heat capacity ρc and thermal conductivity k. These parameters are converted into two new independent thermal properties, the thermal effusivity e and the thermal diffusivity α. This conversion is unique, and can be done vice versa. Therefore, the invented thermal tomography method should preserve all information in the original governing equation.

Having reference now to the drawings, FIG. 1 illustrates a thermal imaging apparatus or system for implementing methods for thermal computed tomography from one-sided pulsed thermal imaging in accordance with the preferred embodiment and generally designated by the reference numeral 100, such as a sample 102 including such as a three layers $L_1$, $L_2$, $L_3$. Thermal imaging system 100 includes a flash lamp 104 providing a pulse of thermal energy for heating a first surface of the sample 102. Thermal imaging system 100 includes, for example, a high-resolution and high-sensitivity infrared camera 106, for example, with 256×256 pixel focal plane array of infrared sensors for taking a rapid series of thermal images of the surface of the article, at a rate which can vary from 100 to 2000 frames per second. Each infrared frame tracks the thermal energy as it passes from the surface through the material. Infrared camera 106 is positioned on the same side of the sample 102 as the flash lamps 104. Thermal imaging system 100 includes a data acquisition and control computer 110 for implementing methods in accordance with the preferred embodiment. Once the infrared data is collected, it is processed to form the 3D images. A major advantage of the method is that the 3D image of an article can be provided in a very short period of time, i.e., a matter of minutes or less.

Figure 2:
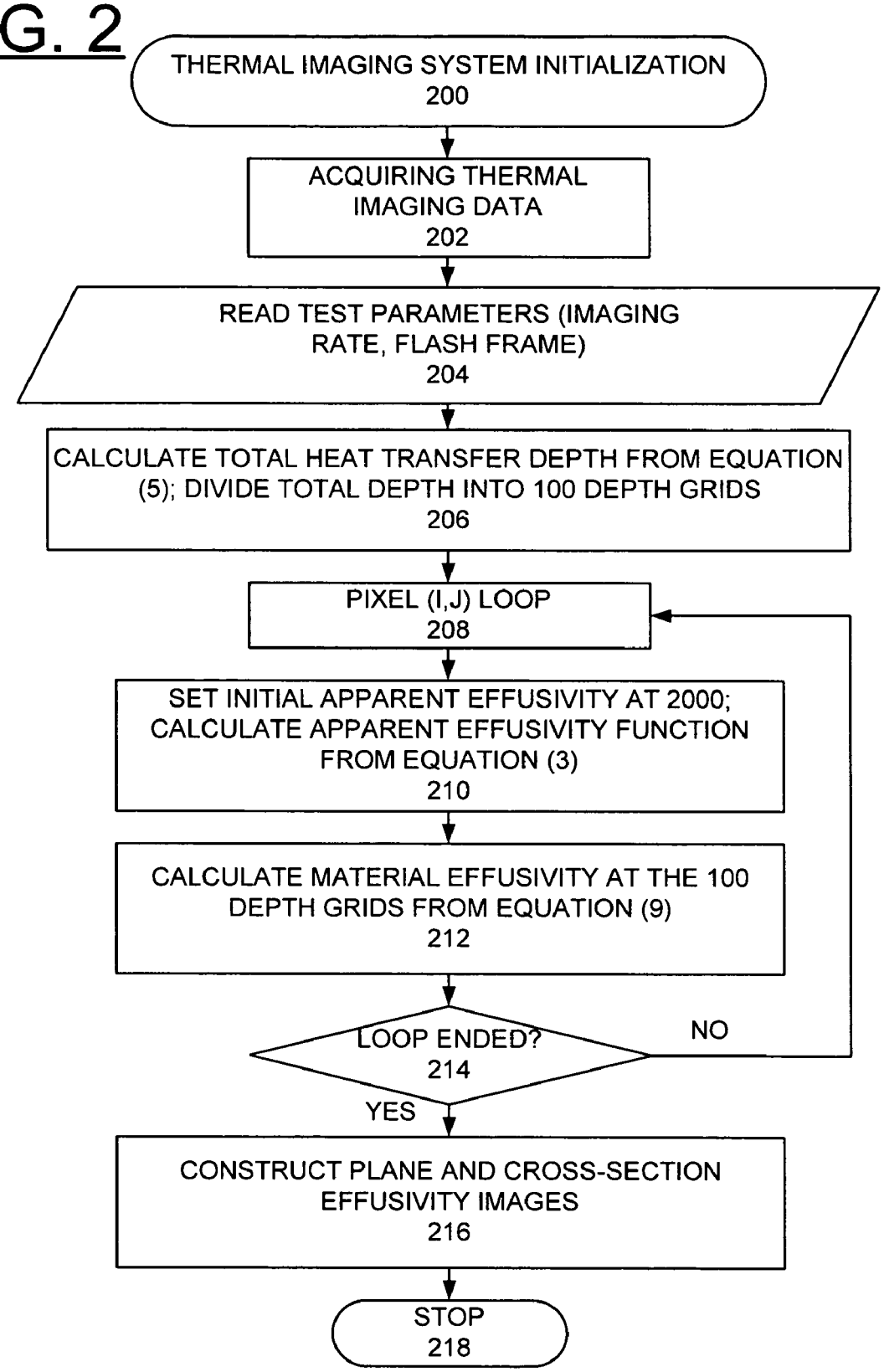
FIG. 2 is a flow chart illustrating exemplary steps for implementing a method for thermal computed tomography from one-sided pulsed thermal imaging in accordance with the preferred embodiment.

Referring now FIG. 2, there are shown exemplary steps for implementing a method for thermal computed tomography from one-sided pulsed thermal imaging in accordance with the preferred embodiment.

As indicated in a block 200, first initialization of the thermal imaging system is preformed and thermal imaging data is acquired as indicated in a block 202. Multiple test parameters are read, for example, imaging rate, flash frame, and the like, as indicated in a block 204. Next a total heat transfer depth is calculated from Eq. (5);

$$z=(\pi\alpha t)^{1/2} \quad (5)$$

and the total depth is divided into 100 depth grids as indicated in a block 206. The number of depth grids can be changed.

A pixel (i,j) loop is obtained as indicated in a block 208, then as indicated in a block 210 an initial apparent effusivity is set at 2000 providing a material effusivity near surface was set to 2000 J/m²-K-s$^{1/2}$. If this material value is known, it can be used. The apparent effusivity function is calculated from Eq. (3);

$$e_a = \frac{Q}{T(t)\sqrt{\pi t}} \quad (3)$$

Next as indicated in a block 212, material effusivity is calculated at the 100 dept grids from Eq. (9)

$$e_n = e(z_n) = ne_a(t_n) - \sum_{i=1}^{n-1} e_i \quad (9)$$

Therefore, a total of 100 plane effusivity images corresponding to these depths are constructed. Then checking whether the loop ended as indicated in a decision block 214. When the loop has not ended, then a next pixel (i,j) loop is obtained at block 208 and the processing continues with the next pixel (i,j) loop. When the loop has ended, then plane and cross-section effusivity images are constructed as indicated in a block 216. This completes the thermal imaging data processing as indicated in a block 218.

Validation Examples

The invented thermal tomography method is validated by using multilayer materials. Multilayered material systems have abrupt changes in material properties. The challenge is to resolve both the abrupt changes between layer boundaries as well as gradual variation of material property within all layers. None of the conventional thermal imaging methods is potentially capable for this challenge. Analysis and imaging of these materials therefore represent the ultimate tests for validating the performance of this thermal tomographic method. Most real inhomogeneous materials (such as skin) exhibit only gradual variation of property along depth, so the performance and accuracy of this method would be better for typical inhomogeneous materials than that for multilayer materials. In the following, several examples are presented to demonstrate the characteristics (uniqueness and stability) of this method. A material system with up to 3 layers, as illustrated in FIG. 1, is used in the calculations. Two sets of material properties, identified as materials no. 1 and 2, are used and listed in Table 1.

TABLE 1

List of thermal properties for two postulated materials used in examples

| Material no. | Conductivity k (W/m-K) | Heat capacity ρc (J/m³-K) | Diffusivity α (mm²/s) | Effusivity e (J/m²-K-s$^{1/2}$) |
|---|---|---|---|---|
| 1 | 2 | 2 × 10⁶ | 1 | 2000 |
| 2 | 1 | 1 × 10⁶ | 1 | 1000 |

First, a single-layer material is evaluated. For this material system, the theoretical solution of surface temperature T(t) from Eq. (4) can be directly used to calculate the apparent effusivity in Eq. (3).

Figure 3A:
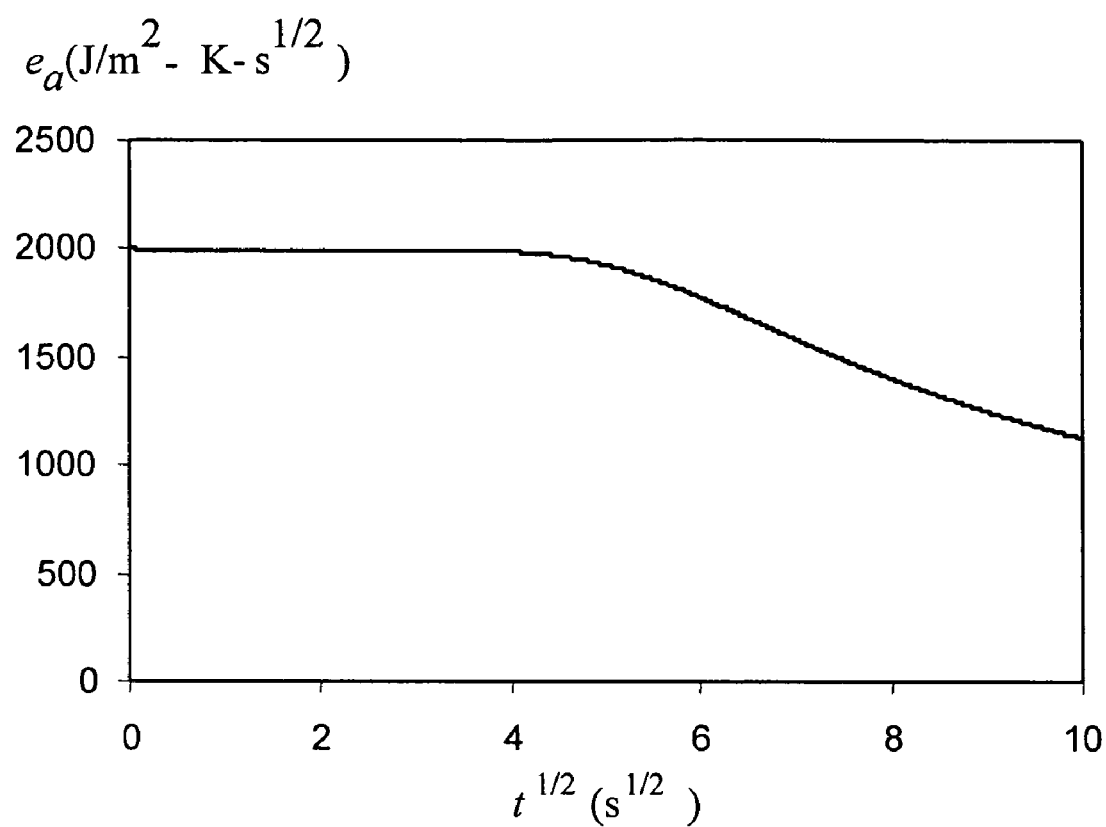
FIGS. 3A and 3B are graphs respectively illustrating surface apparent effusivity as a function of time, based on the thermal properties of a single-layer predefined material with the layer thickness L=10 mm; and the material effusivity predicted by the thermal tomography method from Eq. (9), as a function of depth z for the single-layer predefined material system in accordance with the preferred embodiment.

FIG. 3A shows the surface apparent effusivity as a function of time, based on the thermal properties of the material no. 1 with the layer thickness L=10 mm. The apparent effusivity is constant in early times and decreases in later times, indicating a constant material property up to some depth. However, it does not provide information for 1$^{st}$-layer material thickness and the property of the $2^{nd}$-layer material (in this case, the second layer has no material so its effusivity should be zero).

Figure 3B:
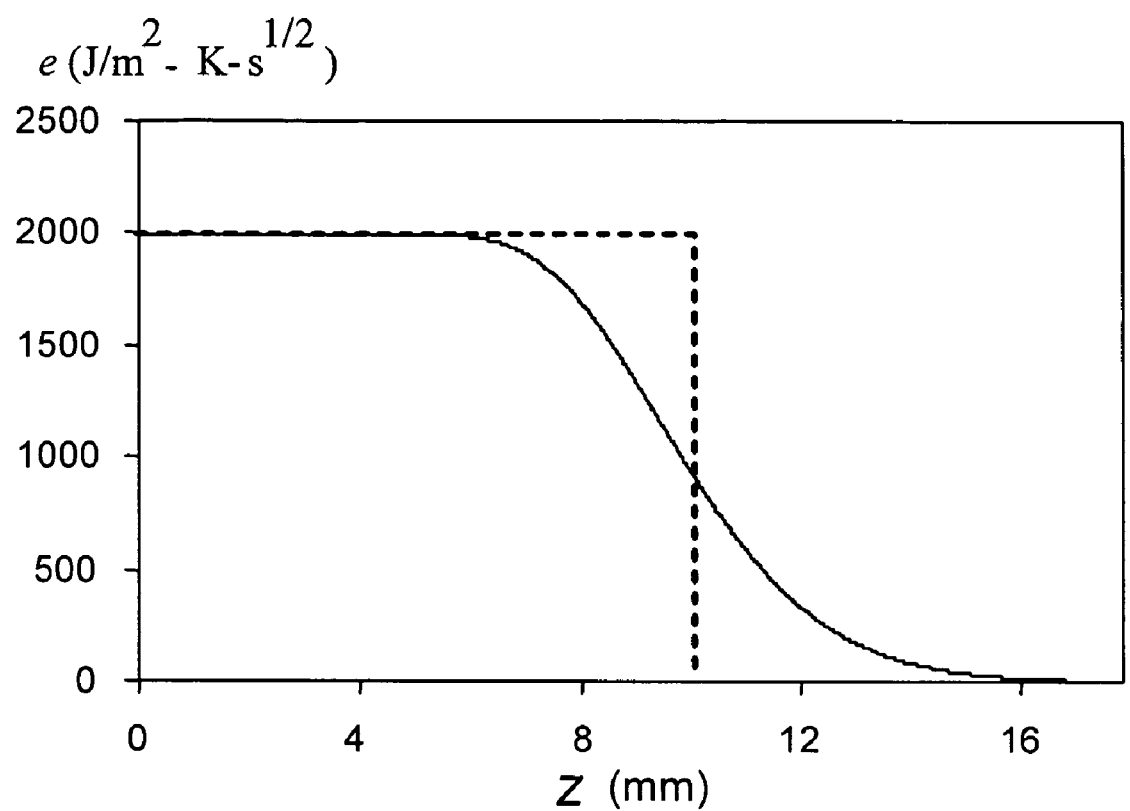

FIG. 3B shows the material effusivity predicted by the thermal tomography method from Eq. (9), as a function of depth z. The dashed rectangular region superimposed in FIG. 3B represents the real material property (effusivity and thickness). It is seen that at the back surface, where z=10 mm, the predicted effusivity does not immediately reduce to zero. This "diffusion" result at a sharp boundary is due to the loss of high-frequency components in the predicted effusivity profile because of the diffusive/dissipative nature of the heat transfer process. The area under the predicted effusivity profile is found to be equal to the area of the dashed rectangle, indicating the conservation of total effusivity from the prediction which further validates the physical postulation used to derive the deconvolution formulation Eq. (9).

Figure 4A:
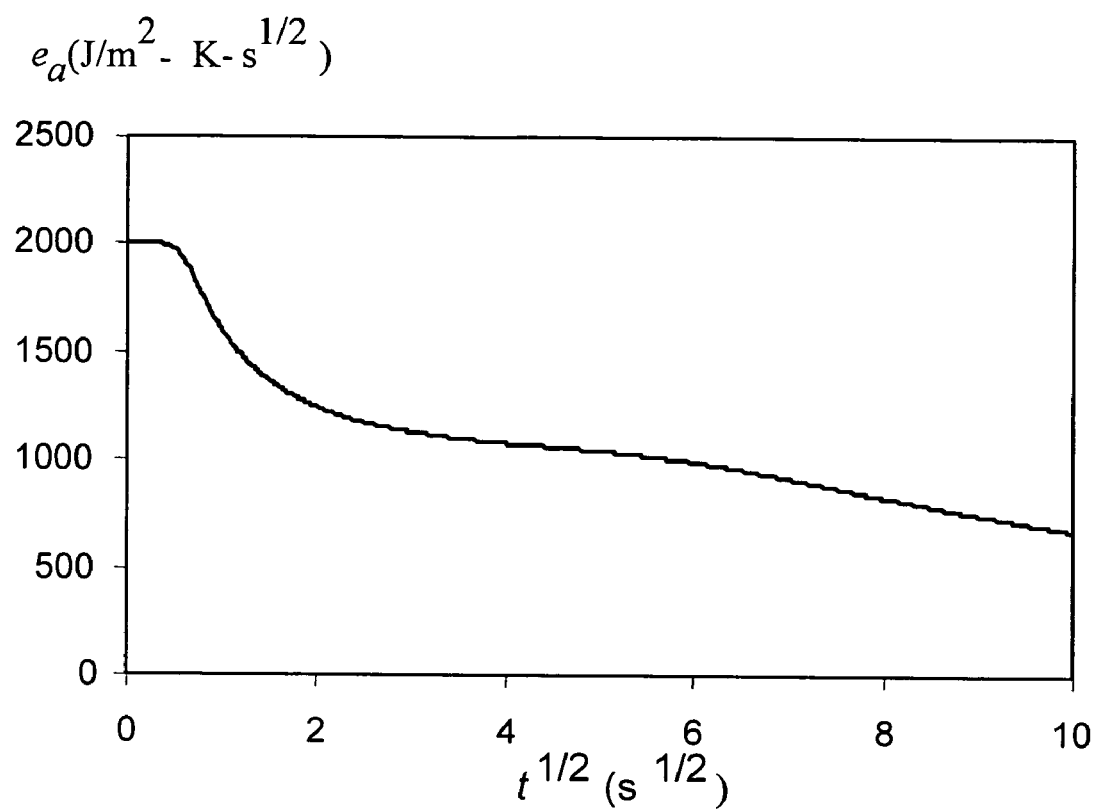
FIGS. 4A and 4B are graphs respectively illustrating surface apparent effusivity as a function of time, based on the thermal properties of a two-layer predefined material system; and the material effusivity predicted by the thermal tomography method from Eq. (9), as a function of depth z for the two-layer predefined material system in accordance with the preferred embodiment.
Figure 4B:
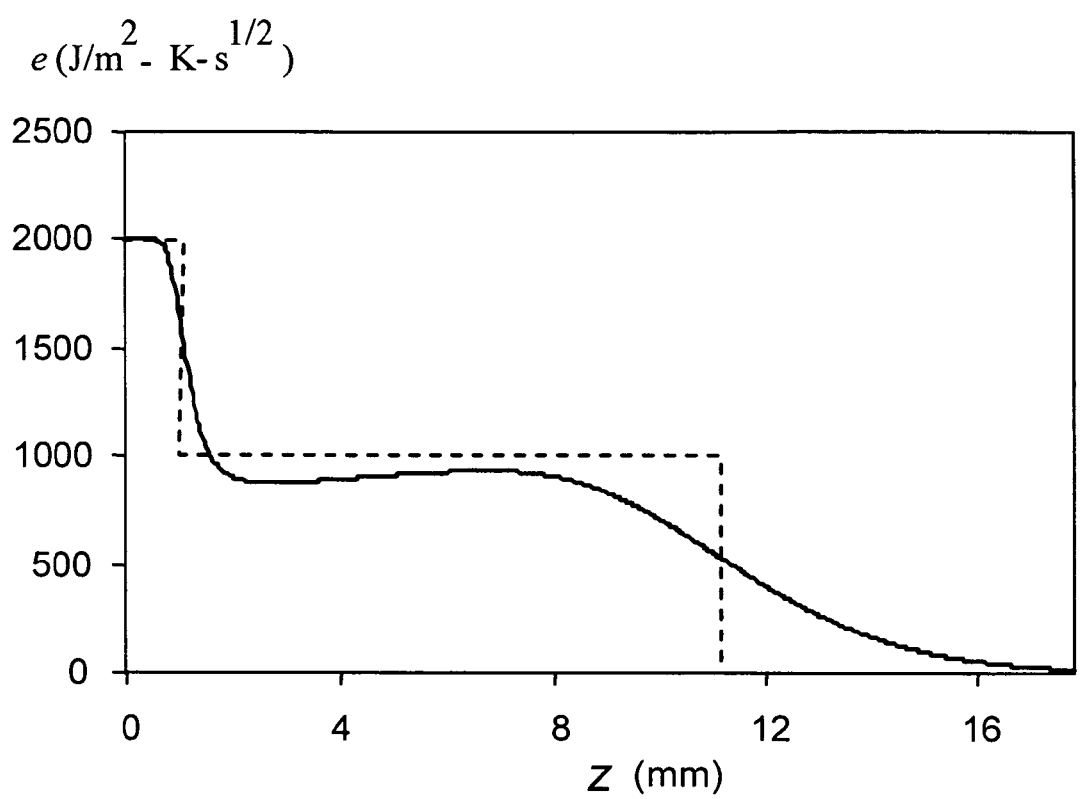

Referring to FIGS. 4A and 4B, a 2-layer material system is evaluated. The first layer contains material no. 1 and the second layer contains material no. 2. The governing equation (1) for the 2-layer system is solved numerically to obtain the surface temperature data T(t) under pulsed thermal imaging condition.

FIG. 4A shows the apparent effusivity calculated from Eq. (3) as a function of time for the 2-layer materials of thicknesses 1 and 10 mm, respectively. Again, the apparent diffusivity does not provide enough information to interpret the material system under study. The predicted material effusivity as a function of depth using the invented thermal tomography method (Eq. 9) is plotted in FIG. 4B, with the material effusivity distribution (dashed line) as a function of depth superimposed in the figure. It is clearly seen that the predicted system consists of two layers: the predicted effusivity is equal to the effusivity of the first-layer material (e=2000 $J/m^2$-K-$s^{1/2}$) within shallow depths and approaches to that of the second-layer material (e=1000 $J/m^2$-K-$s^{1/2}$) after the depth of the first layer (1 mm). The predicted effusivity in the $2^{nd}$ layer first reaches a minimum value at 876 $J/m^2$-K-$s^{1/2}$, indicating that the prediction overshoots the real value of 1000 $J/m^2$-K-$s^{1/2}$ by about 13%. However, as depth increases, the predicted effusivity recovers, and will eventually approach to the exact effusivity of the $2^{nd}$-layer material.

Figure 5:
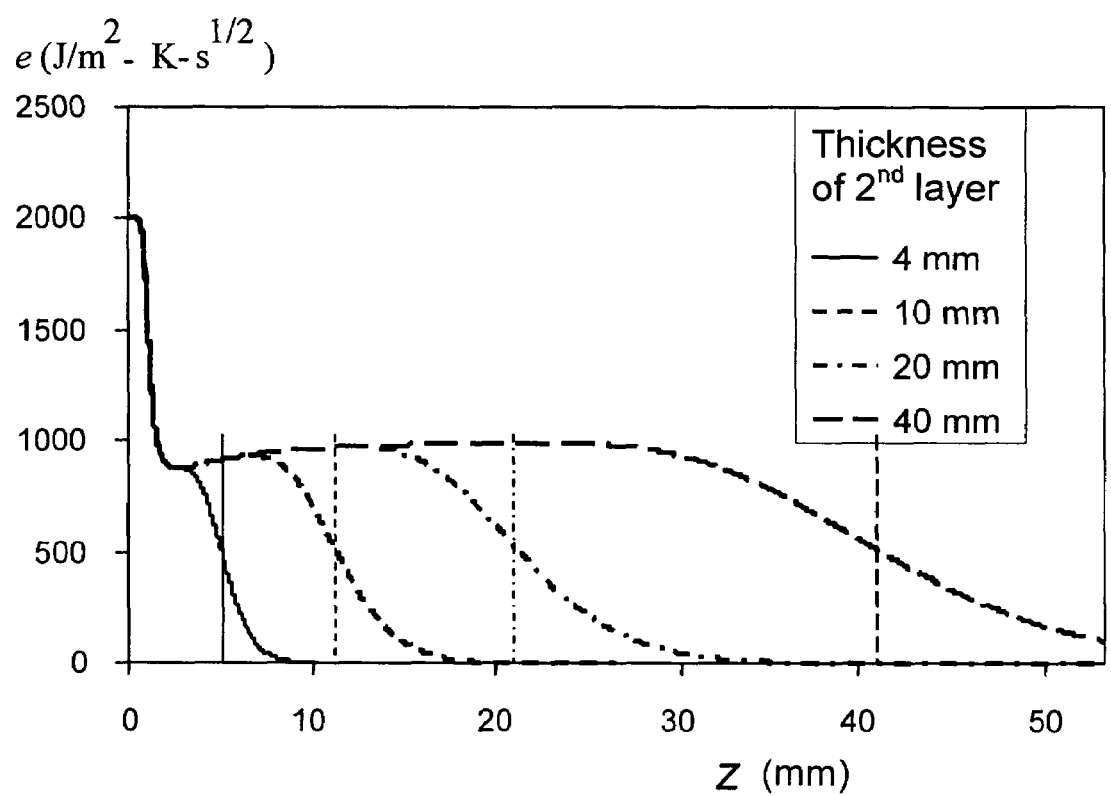
FIG. 5 is a chart illustrating predicted material effusivity profiles as function of depth for 2-layer material systems with various thicknesses in the $2^{nd}$ layer in accordance with the preferred embodiment.

FIG. 5 illustrates the predicted effusivity for several 2-layer material systems with $2^{nd}$ layer thicknesses up to 40 mm. It is seen that the predicted effusivity profile is unique in early times (insensitive to the thickness change of the $2^{nd}$ layer). The exact effusivity of the $2^{nd}$ layer is recovered after the depth of ~20 mm deep, and it remains constant until heat transfer reaches the back surface. This result demonstrates that the deconvolution method, Eq. (9), is robust and stable, and it converges to exact result except near depths of sharp property changes due to the thermal diffusion effect. The diffusion effect appears stronger with the increase of depth.

Figure 6A:
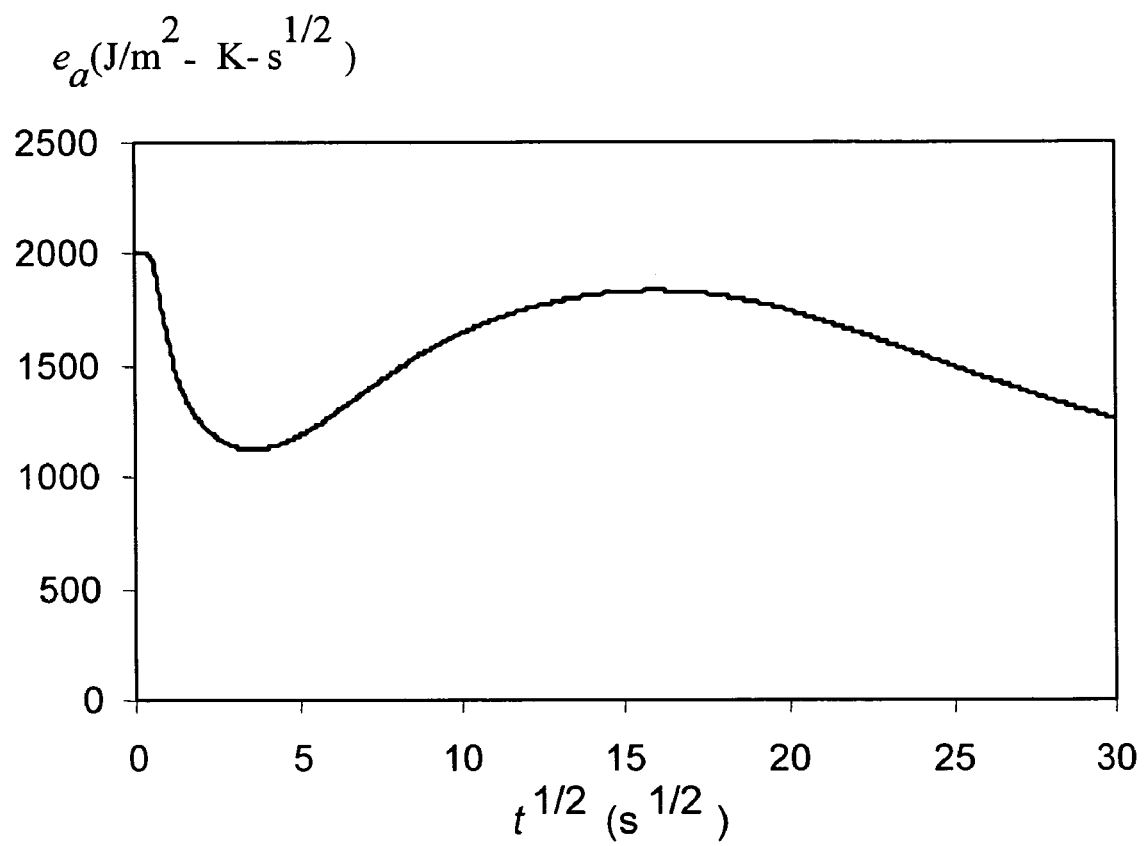
FIGS. 6A and 6B are graphs respectively illustrating surface apparent effusivity as a function of time, based on the thermal properties of a three-layer predefined material system; and the material effusivity predicted by the thermal tomography method from Eq. (9), as a function of depth z for the three-layer predefined material system in accordance with the preferred embodiment.
Figure 6B:
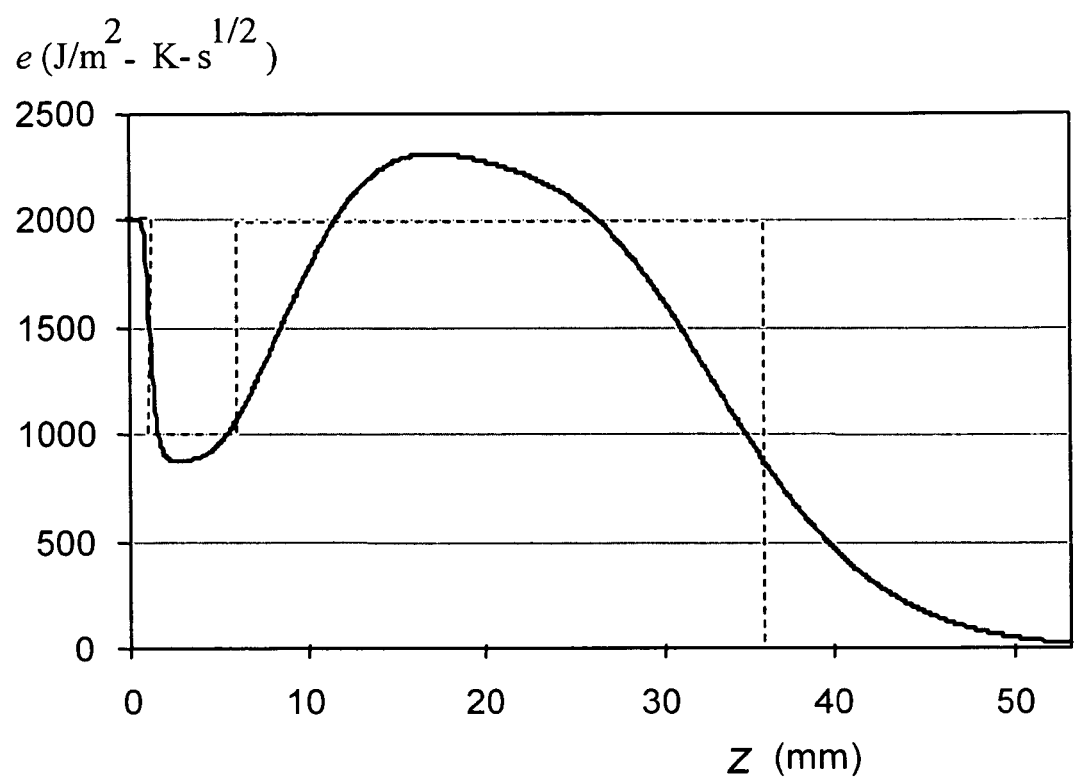

Referring to FIGS. 6A and 6B, a 3-layer material system is evaluated. It is assumed that the $1^{st}$ and $3^{rd}$ layers consist of material no. 1 and the $2^{nd}$ layer consists of material no. 2. Again, the governing equation (1) for the 3-layer system is solved numerically to obtain the surface temperature data T(t) under pulsed thermal imaging condition.

FIG. 6A shows the apparent effusivity calculated from Eq. (3) as a function of time for the 3-layer material system with thicknesses of 1, 5, and 30 mm, respectively, for the three layers. The predicted material effusivity as a function of depth by the invented thermal tomography method (Eq. 9) is plotted in FIG. 6B. The material effusivity distribution is illustrated in dashed line as a function of depth superimposed in FIG. 6B.

FIG. 6B shows that the predicted effusivity within the first 2 layers follows the same trend as that in the 2-layer system shown in FIG. 4B. The predicted effusivity for the $3^{rd}$ layer also exhibits an overshoot to a maximum value of 2310 $J/m^2$-K-$s^{1/2}$, or 15.5% higher than the effusivity of the $3^{rd}$ layer. Again, in deeper depths of the $3^{rd}$ layer, the predicted effusivity will eventually approach to the correct effusivity of the $3^{rd}$-layer material.

Figure 7:
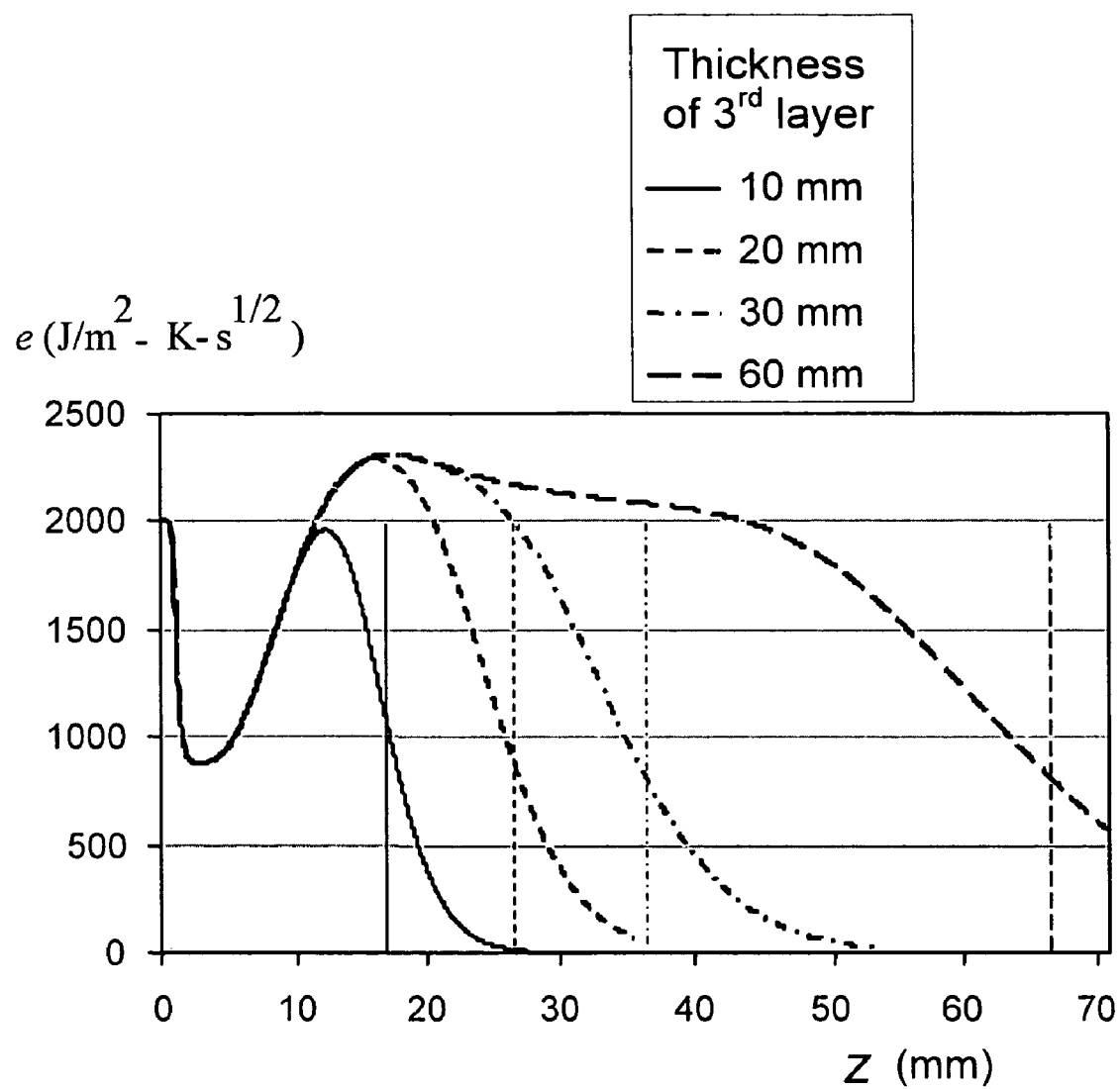
FIG. 7 is a chart illustrating predicted material effusivity profiles as function of depth for 3-layer material systems with various thicknesses in the $3^{rd}$ layer in accordance with the preferred embodiment.

FIG. 7 shows the predicted effusivity profiles with various thicknesses of the $3^{rd}$-layer material. It is seen that the correct effusivity of the $3^{rd}$ layer is obtained at the depth about 45 mm deep, and it remains at that value until nearing the back-surface depth. These results, together with those for one- and two-layer materials, demonstrated the robustness and stability of the deconvolution method developed in this invention.

Figures 8A, 8B:
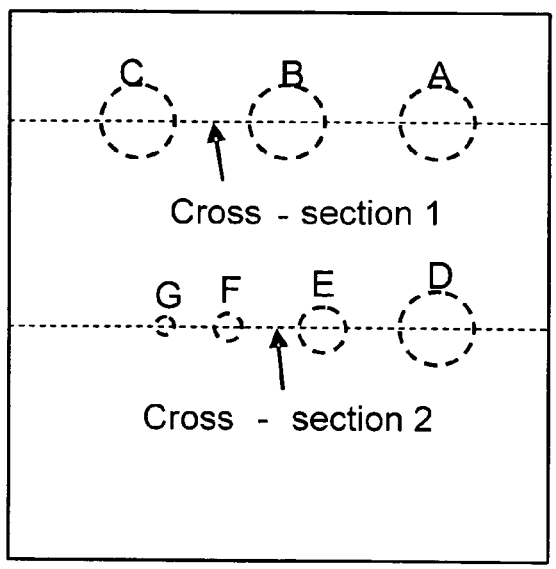
FIGS. 8A and 8B respectively provide a schematic diagram of a sample including first and second cross-sections and a table providing exemplary dimensions for the holes shown in the first and second cross-sections of FIG. 8A in accordance with the preferred embodiment.

FIG. 8A provides a schematic diagram of a sample including first and second cross-sections in a flat-bottom-hole plate. FIG. 8B is a table providing exemplary dimensions for the holes shown in the first and second cross-sections of FIG. 8A of a flat-bottom-hole plate. 3D imaging of a plate sample with flat-bottom holes is illustrated and described with respect to FIGS. 9A and 9B and FIGS. 9C and 9D.

Referring now to FIGS. 9A and 9B and FIGS. 9C and 9D respectively provide predicted thermal effusivity images and diagrams of the first and second cross-sections of FIG. 8A.

A SiC/SiNC ceramic matrix composite plate with machined flat-bottom holes was used to demonstrate 3D imaging performance of the invented thermal tomography method. This plate, illustrated in FIG. 8A and FIGS. 9C and 9D, is 5 cm×5 cm in size, and its thickness varies from 2.3 to 2.7 mm. Seven flat-bottom holes (Holes A-G) of various diameters and depths were machined from the back surface, as illustrated in FIG. 8A. The depths of the holes, listed in FIG. 8B, refer to the distance from the hole bottoms to the front surface where pulsed thermography data were taken. The composite plate was not completely densified so it contains some near-surface defects and distributed porosities.

Pulsed thermography data (surface temperature images) were obtained from the front surface of the plate using a one-sided thermal imaging system 100. The imaging rate was 170 Hz, with a total of 700 frames taken for a test duration of 4.1 s. Thus, at each surface pixel (i,j), its surface temperature $T_{ij}(t)$ was acquired for a total of 700 time steps with a time increment t at 1/170=0.0059 s. The temperature data $T_{ij}(t)$ is converted to the apparent effusivity $e_{aij}(t)$ by Eq. (3), which is then deconvolved into the subsurface material effusivity distribution $e_{ij}(z)$ according to Eqs. (9) and (5). Once $e_{ij}(z)$ for all pixels are calculated and composed together, thermal effusivity distribution in the entire 3D volume of the plate is obtained. The 3D effusivity data are similar to 3D x-ray CT data, which can be sliced in arbitrary planes, such as lateral or cross-sectional slices, to examine the internal material property distribution. The data processing is very fast, for example, typically within a minute for deriving the entire volume data.

Figure 9A:
FIGS. 9A and 9B and FIGS. 9C and 9D respectively provide predicted thermal effusivity images and diagrams of the first and second cross-sections of FIG. 8A in accordance with the preferred embodiment.
Figure 9C:
Figure 9B:
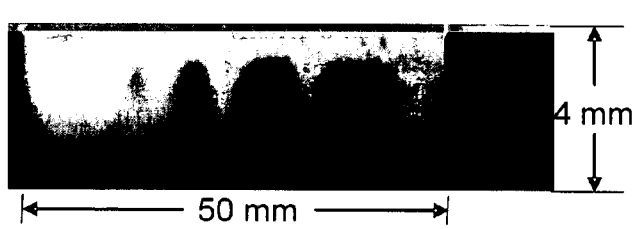
Figure 9D:

FIGS. 9A and 9B show the predicted cross-sectional effusivity images and FIGS. 9C and 9D show corresponding cross-sectional diagrams along the two horizontal lines marked in FIG. 8A. It is seen that all flat-bottom holes are imaged with detailed depth resolution of flat-bottom-hole surfaces. Note that all holes have inclined bottom surface due to a machining error. In addition, many shallow defects, darker spots, are resolved with good image resolution. These defects are small voids due to incomplete densification of the plate. However, the effusivity images in FIGS. 9A and 9B show clearly the degradation of spatial resolution with depth due to the 3D diffusion effect, and a slightly lower effusivity prediction just under surface because of the finite flash duration effect, flash duration effect easily can be corrected. Nevertheless, this invented thermal tomography method provides the first effective 3D imaging method based on pulsed thermography and the result is already superior than any other thermal imaging methods currently available.

From the examples presented, it is demonstrated that the thermal tomographic method developed in this invention is robust and stable and produces unique results. The predicted effusivity value always converges to the exact material effusivity in depth regions of constant properties. The prediction deviates from exact solution near depths with abrupt property changes. This is represented by a gradual transition, due to loss of the high-frequency components, followed by an overshoot of the predicted effusivity at a sharp boundary (this problem is common to all tomographic techniques). The maximum overshoot error is less than 16% for the examples presented above. However, there is no overshoot in regions of zero effusivity (i.e., outside material after passing the back surface). These favorable characteristics are attributed to the high stability of the deconvolution scheme from this thermal tomography method. The robustness and stability of this method also allows for future implementation of diffusion/dissipation reduction schemes that usually introduce some instability because they attempt to recover the higher-frequency components in the solution. Nevertheless, without any modification, this invented method can be directly used for tomographic reconstruction of various different layered and inhomogeneous materials. Examples of these material systems include skin/tissue and composite materials. Currently, no other thermal imaging method can determine property distribution under surface for layered and/or inhomogeneous materials.

In brief summary, the invented thermal tomographic method is the first practical method capable of 3D imaging of material's interior. 3D imaging solves all deficiencies in conventional 2D thermal imaging methods, which are limited to detecting only one dominant defect under surface and requiring specific models in data processing/interpretation for specific material systems. It was demonstrated to imaging the entire 3D volume of a ceramic matrix composite plate with flat-bottom holes machined from a back surface. All defects within the plate were detected with high sensitivity and resolution, especially near the subsurface region. The data processing for constructing the entire 3D image is very fast, typically less than a minute for a large data set. Because the imaged parameter is a material property (thermal effusivity), the image data can be easily interpreted, for example, see FIGS. 9A and 9B. While in conventional thermal imaging methods, the final image data are mostly based on the measured surface temperature T(t) (such as its derivatives), interpretation of these data is not straight forward and requires knowledge of fundamental thermal imaging theories. In addition, this method does not require calibration and is fully automated, so an operator does not need any formal training to use it.

While the present invention has been described with reference to the details of the embodiments of the invention shown in the drawing, these details are not intended to limit the scope of the invention as claimed in the appended claims.

What is claimed is:

1. A computer-implemented method for automated thermal computed tomography from one-sided pulsed thermal imaging comprising:
   acquiring experimental thermal imaging data;
   calculating material effusivity at a set number of depth grids using the acquired experimental thermal imaging data; and
   constructing a plurality of plane effusivity images corresponding to the calculated material effusivity at said set number of depth grids.

2. A computer-implemented method for automated thermal computed tomography as recited in claim 1 wherein acquiring experimental thermal imaging data includes utilizing an infrared camera, acquiring a series of thermal images responsive to a pulse of thermal energy for heating a first surface of the sample.

3. A computer-implemented method for automated thermal computed tomography as recited in claim 2 wherein acquiring said series of thermal images includes said series of thermal images at a selected rate, said selected rate within a range of 100 to 2000 frames per second.

4. A computer-implemented method for automated thermal computed tomography as recited in claim 2 wherein acquiring said series of thermal images includes tracking the thermal energy passing from the surface through the material.

5. A computer-implemented method for automated thermal computed tomography as recited in claim 1 wherein calculating material effusivity at a set number of depth grids using the acquired experimental thermal imaging data includes converting measured surface temperature into an apparent effusivity, said apparent effusivity being related to thermal effusivity of an interior of the sample.

6. A computer-implemented method for automated thermal computed tomography as recited in claim 5 wherein determining a thermal effusivity, said thermal effusivity represented by $e=(\rho c k)^{1/2}$ wherein $\rho$ represents density, c represents specific heat, k represents thermal conductivity.

7. A computer-implemented method for automated thermal computed tomography as recited in claim 1 wherein constructing a plurality of plane effusivity images includes identifying a relationship between depth and time to determine a speed of heat propagation.

8. A computer-implemented method for automated thermal computed tomography as recited in claim 7 wherein said relationship is represented by $z=(\pi \alpha t)^{1/2}$ wherein $\alpha$ represents thermal diffusivity, t represents time.

9. A computer-implemented method for automated thermal computed tomography as recited in claim 1 wherein calculating material effusivity at a set number of depth grids using the acquired experimental thermal imaging data includes calculating a material effusivity function represented by $$e_n = e(z_n) = n e_a(t_n) - \sum_{i=1}^{n-1} e_i$$

where $e_n = e(z_n)$ represents a spatial distribution function of thermal effusivity for the sample.

10. A computer-implemented method for automated thermal computed tomography as recited in claim 1 wherein calculating material effusivity at a set number of depth grids using the acquired experimental thermal imaging data includes providing an initial value of apparent effusivity for the sample.

11. A computer-implemented method for automated thermal computed tomography as recited in claim 1 wherein acquiring experimental thermal imaging data includes reading a predefined test parameter.

12. A computer-implemented method for automated thermal computed tomography as recited in claim 11 wherein reading a predefined test parameter includes reading an imaging rate.

13. A computer-implemented method for automated thermal computed tomography as recited in claim 11 wherein reading a predefined test parameter includes reading a flash frame.

14. Apparatus for automated thermal computed tomography from one-sided pulsed thermal imaging of a sample comprising:
   a flash lamp applying a pulse of thermal energy for heating the first surface of the sample
   an infrared camera acquiring a series of thermal images responsive to said pulse of thermal energy for heating the first surface of the sample;
   a data acquisition and control computer, said data acquisition and control computer calculating material effusivity at a set number of depth grids using the acquired experimental thermal imaging data; and constructing a plurality of plane effusivity images corresponding to the calculated material effusivity at said set number of depth grids.

15. Apparatus for automated thermal computed tomography as recited in claim 14 wherein the acquired experimental thermal imaging data includes temporal surface temperature data, and wherein said data acquisition and control computer converts the temporal surface temperature data into a spatial depth distribution of thermal effusivity.

16. Apparatus for automated thermal computed tomography as recited in claim 14 wherein said infrared camera acquiring a series of thermal images includes said infrared camera acquiring said series of thermal images at a selected rate, said selected rate within a range of 100 to 2000 frames per second.

17. Apparatus for automated thermal computed tomography as recited in claim 14 wherein said data acquisition and control computer determines a thermal effusivity, said thermal effusivity represented by $e=(\rho ck)^{1/2}$ wherein $\rho$ represents density, c represents specific heat, k represents thermal conductivity.

18. Apparatus for automated thermal computed tomography as recited in claim 14 wherein said data acquisition and control computer identifies a relationship between depth and time to determine a speed of heat propagation for constructing a plurality of plane effusivity images.

19. Apparatus for automated thermal computed tomography as recited in claim 18 wherein said relationship is represented by $z=(\pi\alpha t)^{1/2}$ wherein $\alpha$ represents thermal diffusivity, t represents time.

20. Apparatus for automated thermal computed tomography as recited in claim 14 wherein said data acquisition and control computer calculates a material effusivity function represented by $$e_n = e(z_n) = ne_a(t_n) - \sum_{i=1}^{n-1} e_i$$

where $e_n = e(z_n)$ represents a spatial distribution function of thermal effusivity for the sample.

* * * * *